United States Patent
Okuno et al.

(10) Patent No.: US 9,668,708 B2
(45) Date of Patent: Jun. 6, 2017

(54) X-RAY IMAGING DEVICE

(71) Applicant: SHIMADZU CORPORATION, Kyoto (JP)

(72) Inventors: Tomoharu Okuno, Kyoto (JP); Shinji Hamasaki, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 161 days.

(21) Appl. No.: 14/766,522

(22) PCT Filed: Feb. 27, 2013

(86) PCT No.: PCT/JP2013/055155
§ 371 (c)(1),
(2) Date: Aug. 7, 2015

(87) PCT Pub. No.: WO2014/132362
PCT Pub. Date: Sep. 4, 2014

(65) Prior Publication Data
US 2016/0015342 A1    Jan. 21, 2016

(51) Int. Cl.
*H05G 1/02* (2006.01)
*A61B 6/00* (2006.01)
(Continued)

(52) U.S. Cl.
CPC .............. *A61B 6/4405* (2013.01); *A61B 6/06* (2013.01); *A61B 6/105* (2013.01); *A61B 6/4283* (2013.01);
(Continued)

(58) Field of Classification Search
CPC ... A61B 6/4283; A61B 6/4494; A61B 6/4405; A61B 6/4233; A61B 6/06; A61B 6/4452; A61B 6/105; G03B 42/08; G03B 42/02
(Continued)

(56) References Cited

U.S. PATENT DOCUMENTS

2010/0329426 A1* 12/2010 Oda .................... A61B 6/4283
                                                                 378/98.2
2010/0329427 A1    12/2010 Takae et al.
2012/0045037 A1*  2/2012 Carmichael .......... A61B 6/4266
                                                                 378/198

FOREIGN PATENT DOCUMENTS

JP    2000-70244    3/2000
JP    2004-73354    3/2004
(Continued)

OTHER PUBLICATIONS

PCT/JP2013/055155 Search Report mailed Apr. 2, 2013, 2 pages—English; 2 pages—Japanese.

*Primary Examiner* — Courtney Thomas
(74) *Attorney, Agent, or Firm* — Andrew F. Young, Esq.; Lackenbach Siegel, LLP

(57) ABSTRACT

When an X-ray detector is removed from a storage part, a sensor senses this, and transmits to an up and down control part a signal indicating that the X-ray detector has been taken out of the storage part. Upon receipt of the signal, the up and down control part releases braking force by electro permanent magnets. In doing so, sticking force of the electro permanent magnet on a fixing part, and sticking force of the electro permanent magnet on a stopper plate are released. The weight of a counter weight is larger than the total value of the weights of the arm, X-ray tube, collimator, and the like, and therefore in a state where the arm is released from being fixed by the electro permanent magnets, the arm starts to move up together with the X-ray tube and the collimator.

10 Claims, 9 Drawing Sheets

(51) Int. Cl.
*A61B 6/06* (2006.01)
*A61B 6/10* (2006.01)

(52) U.S. Cl.
CPC ............ *A61B 6/447* (2013.01); *A61B 6/4429* (2013.01); *A61B 6/4452* (2013.01); *A61B 6/4476* (2013.01); *A61B 6/54* (2013.01)

(58) Field of Classification Search
USPC .................................................. 378/193–198
See application file for complete search history.

(56) References Cited

FOREIGN PATENT DOCUMENTS

| | | |
|---|---|---|
| JP | 2004-275584 | 10/2004 |
| JP | 2006-43274 | 2/2006 |
| JP | 2007-000535 | 1/2007 |
| JP | 2011-167296 | 9/2011 |
| WO | WO2009/104656 | 8/2009 |

\* cited by examiner

X-RAY IMAGING DEVICE

CROSS REFERENCE TO RELATED APPLICATIONS

This application relates to and claims priority from Ser. No. PCT/JP2013/055155 filed Feb. 27, 2013, the entire contents of each of which are incorporated herein by reference.

TECHNICAL FIELD

The present invention relates to an X-ray imaging apparatus, and more particularly, to an X-ray imaging apparatus for rounds, which is intended to go the rounds of hospital rooms to take images.

BACKGROUND ART

Such an X-ray imaging apparatus for rounds is configured to electrically move among hospital rooms by disposing an X-ray tube and a collimator at the fore end of an arm movable up and down along a supporting post disposed on a cart and driving a motor provided in the cart (see Patent Literature 1). In such an X-ray imaging apparatus for rounds, when moving among hospital rooms, the arm is moved down along the supporting post, and fixed by a fixing mechanism at a fixing position where the arm comes into abut with a fixing part called an arm catch. On the other hand, when taking X-ray images, an operator operates a fixation release button to thereby release the fixation of the arm, and moves up the arm together with the X-ray tube and the collimator to arrange the X-ray tube and the like at positions suitable for X-ray imaging.

CITATION LIST

Patent Literature

[Patent Literature 1] JP-A2007-535

SUMMARY OF INVENTION

Technical Problem

As described, in the X-ray imaging apparatus for rounds, when starting X-ray imaging, an operator is required to perform operations for releasing the fixation state by operating the arm fixation release button, and then moving up the arm together with the X-ray tube and the like. For this reason, it takes time for the operations, burdening the operator.

The present invention is made in order to solve the above-described problem, and intends to provide an X-ray imaging apparatus capable of automatically release fixation of an arm to quickly prepare X-ray imaging.

Solution to Problem

According to a first aspect of the present invention, an X-ray imaging apparatus for a round includes: a cart; a supporting post that is disposed on the cart; an arm that is movable up and down along the supporting post; an X-ray tube that is disposed on the arm; an X-ray detector that detects an X-ray that is irradiated from the X-ray tube and passes through a subject; and a storage part for the X-ray detector, and the X-ray imaging apparatus includes: a fixing mechanism that fixes the arm at a fixing position that is a position where the arm should be arranged when moving the cart and lower than a height position where an X-ray image is taken; a storage detector that detects that the X-ray detector has been taken out of the storage part; and an up and down control part that when the storage detector detects that the X-ray detector has been taken out of the storage part, releases the arm from being fixed by the fixing mechanism.

A second aspect according to the present invention, in the first aspect of the present invention, includes an arm driving mechanism that when the arm is released from being fixed by the fixing mechanism, moves up the arm from the fixing position.

A third aspect according to the present invention, in the second aspect of the present invention, includes a collimator that is disposed on the arm, in which the arm driving mechanism includes: a pulley that is disposed in the supporting post; a counter weight that has weight larger than a total value of weights of the arm, the X-ray tube, and the collimator; and a cable that is wound around the pulley, and has one end connected to the arm and the other end connected to the counter weight.

A fourth aspect according to the present invention, in the third aspect of the present invention, further includes a height position detector that detects a height position of the arm, in which after the up and down control part has released the arm from being fixed by the fixing mechanism, when the height position of the arm detected by the height position detector reaches a predetermined position, the up and down control part again fixes the arm by the fixing mechanism.

A fifth aspect according to the present invention, in the third aspect of the present invention, in which after a certain time has passed since the up and down control part released the arm from being fixed by the fixing mechanism, the up and down control part again fixes the arm by the fixing mechanism.

A sixth aspect according to the present invention, in the second aspect of the present invention, in which: the arm driving mechanism includes a motor that drives the arm up and down; and when the arm is released from being fixed by the fixing mechanism, the up and down control part moves up the arm from the fixing position a predetermined distance by controlling rotation of the motor.

A seventh aspect according to the present invention, in the any of the first to sixth aspects of the present invention, in which the fixing mechanism includes an electro permanent magnet mechanism that has a permanent magnet and an electromagnet, and by generating braking force against up and down movement of the arm with use of magnetic force of the permanent magnet, and also applying current to a coil of the electromagnet to thereby make the electromagnet generate magnetic force that cancels out the magnetic force of the permanent magnet, releases the braking force against the up and down movement of the arm by the permanent magnet.

Advantageous Effects of Invention

According to the first aspect of the present invention, when the X-ray detector is taken out for X-ray imaging, the fixing state of the arm is automatically released, and consequently the X-ray imaging can be quickly prepared.

According to the second to sixth aspects of the present invention, when the arm is released from being fixed, the action of the arm driving mechanism automatically moves up the arm from the fixing position, and consequently the X-ray imaging can be more quickly prepared.

According to the seventh aspect of the present invention, the action of the electro permanent magnet mechanism can easily fix the arm or release the fixation.

DESCRIPTION OF EMBODIMENTS

Figure 1:
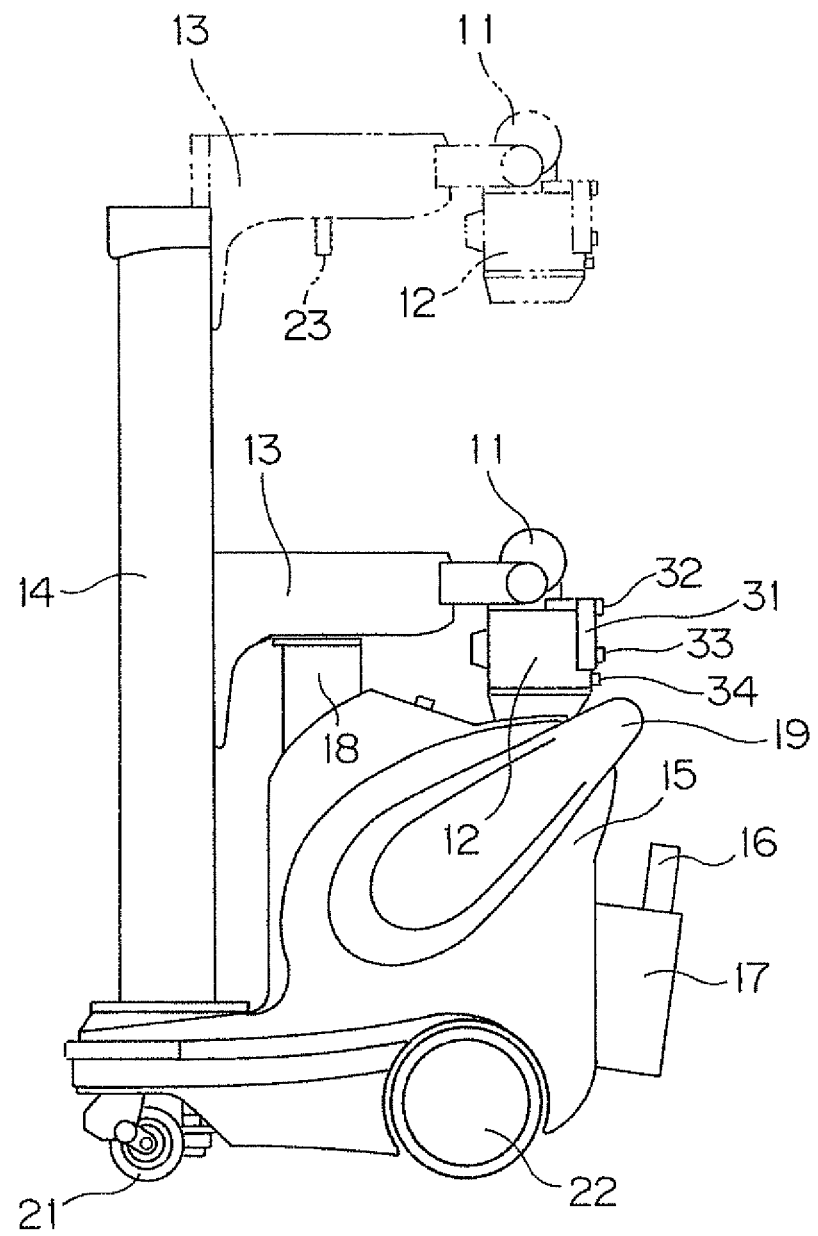
FIG. 1 is a side view of an X-ray imaging apparatus according to the present invention.
Figure 2:
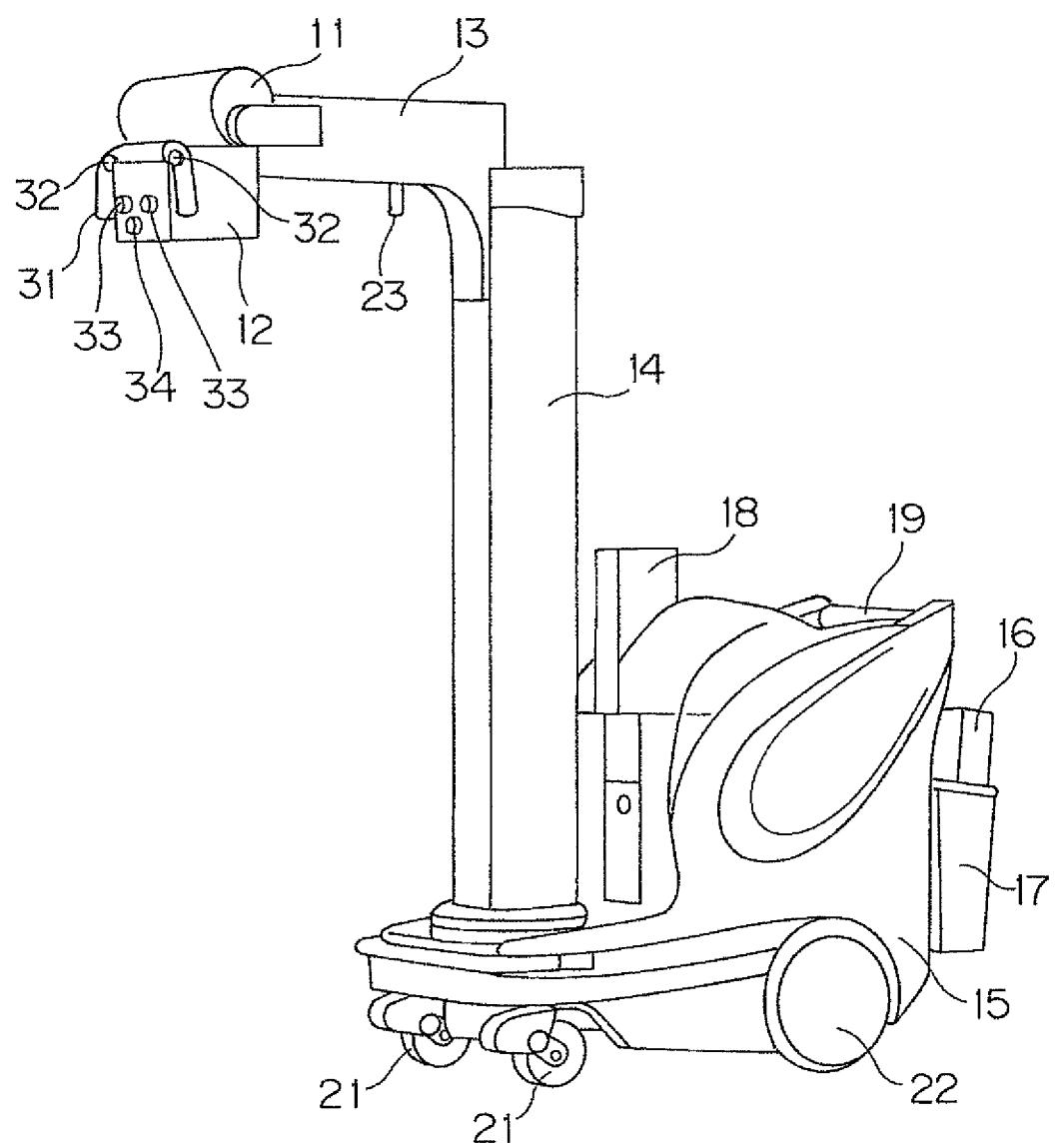
FIG. 2 is a perspective view of the X-ray imaging apparatus according to the present invention.

Embodiments of the present invention will hereinafter be described on the basis of the drawings. FIG. 1 is a schematic side view of an X-ray imaging apparatus according to the present invention. Also, FIG. 2 is a perspective view of the X-ray imaging apparatus according to the present invention.

The X-ray imaging apparatus includes: a supporting post 14 disposed on a cart 15; am arm 13 disposed movably up and down along the supporting post 14; an X-ray tube 11 disposed at the fore end of the arm 13; a collimator 12 disposed below the X-ray tube 11; an X-ray detector 16 for detecting X-rays that are irradiated from the X-ray tube 11 and pass through a subject; and a storage part 17 for storing the X-ray detector 16. Further, the X-ray imaging apparatus includes: a pair of left and right front wheels 21 serving as wheels for changing a direction; a pair of left and right rear wheels 22 serving as wheels for driving; and an operation handle 19 for operating a traveling direction of the cart 15.

The arm 13 is adapted to be movable up and down between a fixing position that is indicated by a solid line in FIG. 1 and a position where the arm 13 should be arranged when moving the cart 15 and an imaging position that is positioned upward from the fixing position. When the arm 13 remains at the fixing position, the lower surface of the arm 13 comes into abut with a fixing part 18 called an arm catch. In this state, a pin 23 disposed on the lower surface of the arm 13 is stored in a hole part (not illustrated) formed in the fixing part 18. Also, as illustrated in FIG. 2, the arm 13 turns around the supporting post 14 in a state of being moved up from the fixing position.

On the front surface of the collimator 12, a pair of dials 33 for opening/closing collimator leaves, and a button 34 for lighting a collimator lamp used to confirm an X-ray irradiation field are disposed. Also, the collimator 12 is provided with a handle 31 that is used when moving the X-ray tube 11 and the collimator 12. Further, the handle 31 is provided with a pair of release buttons 32 for releasing the arm 13 from being fixed by the fixing mechanism adapted to inhibit the arm 13 from moving up or down, or turning.

Figure 3:
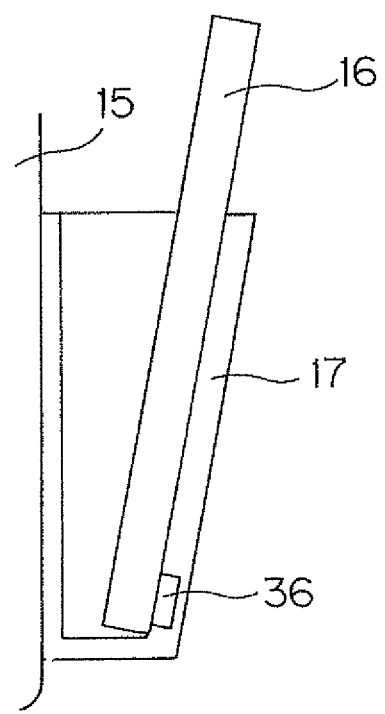
FIG. 3 is a side cross-sectional view illustrating a storage part 17 for storing an X-ray detector 16.

FIG. 3 is a side cross-sectional view illustrating the storage part 17 for storing the X-ray detector 16.

The storage part 17 is a part for inserting the X-ray detector 16 such as a flat panel detector from above to store the X-ray detector 16. In the lower part of the storage part 17, a sensor 36 that is configured as a proximity switch, a micro switch, or the like and for confirming whether or not the X-ray detector 16 is present is disposed. The sensor 36 functions as a storage detector adapted to detect that the X-ray detector 16 has been taken out of the storage part 17.

Figure 4:
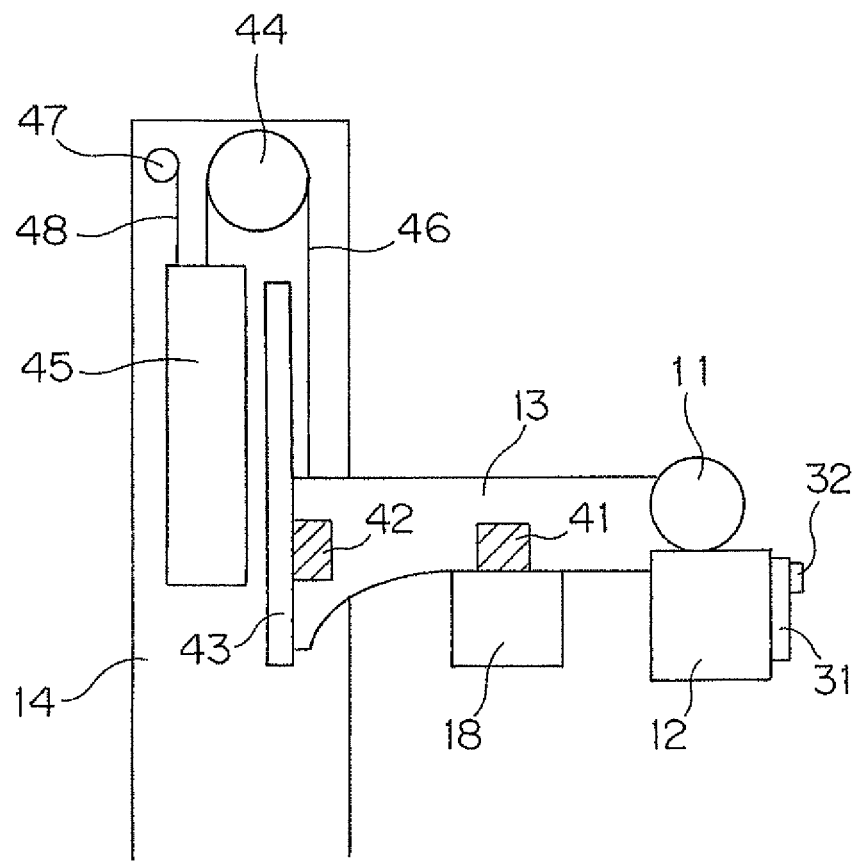
FIG. 4 is a schematic diagram illustrating an arm driving mechanism for moving up an arm 13 and a fixing mechanism for fixing the arm 13, both of which are according to a first embodiment of the present invention and employed for the X-ray imaging apparatus.

FIG. 4 is a schematic diagram illustrating an arm driving mechanism for moving up the arm 13 and a fixing mechanism for fixing the arm 13, both of which are according to a first embodiment of the present invention and employed for the X-ray imaging apparatus.

The arm driving mechanism for moving up the arm 13 includes: a pulley 44 that is rotatably disposed at the upper end inside the supporting post 14; a counter weight 45 that is movable up and down inside the supporting post 14; and a wire 46 of which one end is connected to the arm 13 and the other end is wound around the pulley 44 in a state of being connected to the counter weight 45. Note that in place of the wire 48, another cable such as a belt or a chain may be used. The weight of the counter weight 45 is one larger than the total value of the weights of the arm 13, X-ray tube 11, collimator 12, and the like. Also, the counter weight 45 is connected to a potentiometer 47 via a wire 48. The height positions of the arm 13 and the counter weight 45 are measured by the potentiometer 47.

Inside the supporting post 14, a stopper plate 43 extending in a vertical direction is disposed. Also, at a position on the arm 13 side facing the stopper plate 43, an electro permanent magnet 42 is disposed. Further, at a position on the arm side 13 facing the fixing part 18, an electro permanent magnet 41 is disposed. These electro permanent magnets 41 and 42 function as the fixing mechanism for fixing the arm 13 at a predetermined position.

Figure 5:
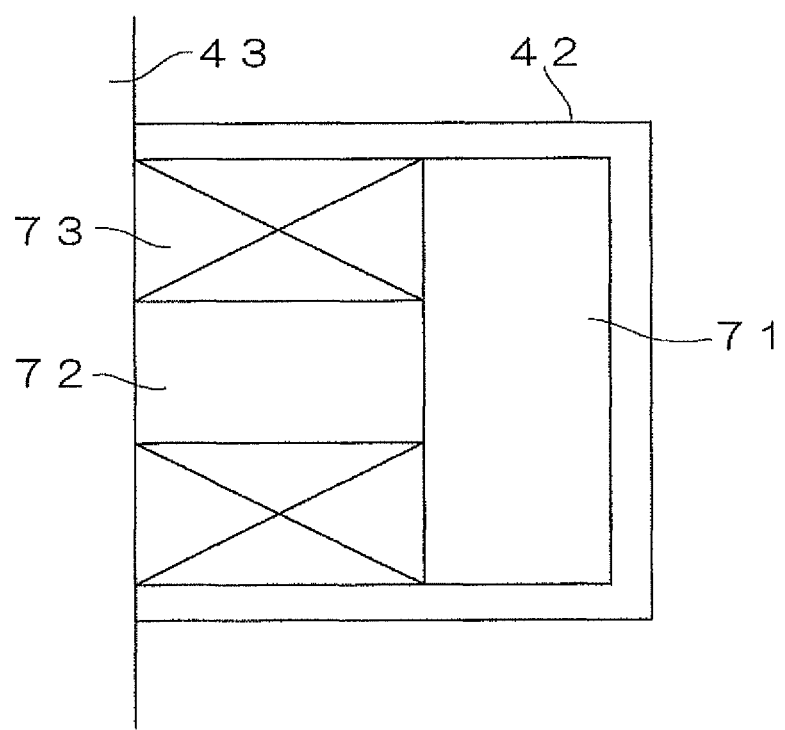
FIG. 5 is a schematic diagram of an electro permanent magnet 42.
Figure 6:
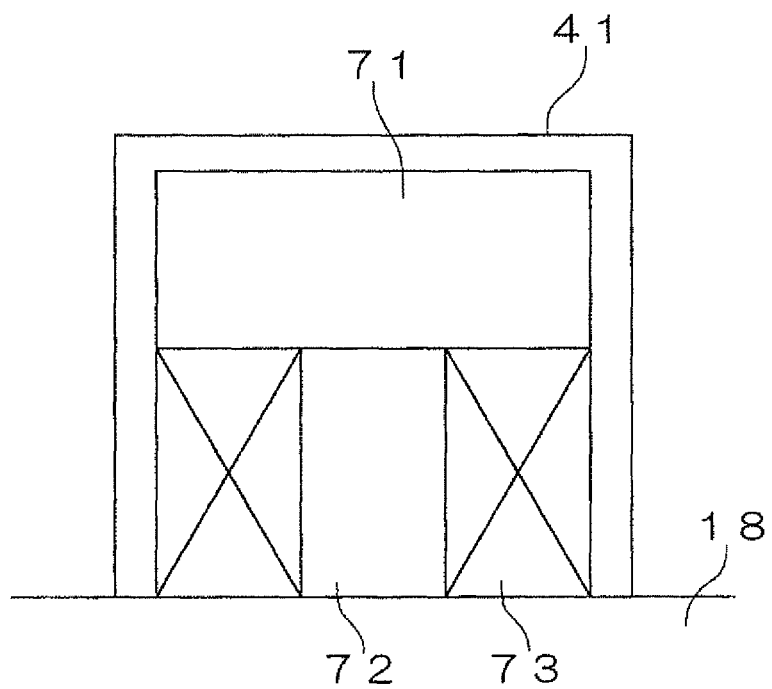
FIG. 6 is a schematic diagram of an electro permanent magnet 41.

FIG. 5 is a schematic diagram of the above-described electro permanent magnet 42. Also, FIG. 6 is a schematic diagram of the above-described electro permanent magnet 41.

Each of the electro permanent magnets 41 and 42 is configured to include a permanent magnet 71, an iron core 72, and a coil 73 disposed around the iron core 72. In a state where currents do not flow through the coils 73, the electro permanent magnets 41 and 42 fulfill functions as magnets by the actions of the permanent magnets 71, respectively. In this case, the electro permanent magnet 41 sticks fast to the fixing part 18, and the electro permanent magnet 42 sticks fast to the stopper plate 43, whereby braking force is generated to restrict the arm 13 from moving. On, the other hand, in the case where an operator operates the above-described release buttons 32 or performs another operation, and thereby applies currents to the coils 73 as parts of electromagnets to make the electromagnets generate magnetic forces that cancel out magnetic forces of the permanent magnets 71, respectively, the braking force is released by the actions of the permanent magnets 71, thus making it possible to move the arm 13.

Figure 7:
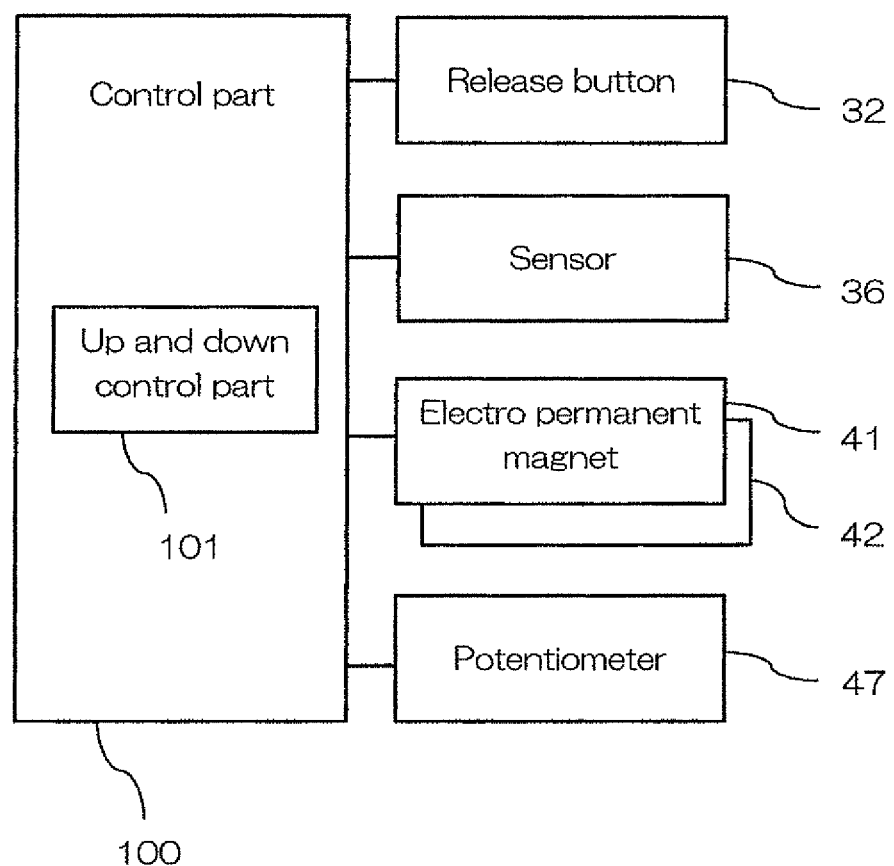
FIG. 7 is a block diagram illustrating a main control system of the X-ray imaging apparatus according to the first embodiment of the present invention.

FIG. 7 is a block diagram illustrating a main control system of the X-ray imaging apparatus according to the first embodiment of the present invention.

The X-ray imaging apparatus has a control part 100 configured to include: an ROM that stores an operation program necessary to control the apparatus; an RAM that temporarily stores data or the like at the time of the control; a CPU that executes a logical operation; and the like. The control part 100 controls the whole of the X-ray imaging apparatus including the above-described X-ray tube 11 and collimator 12. As illustrated in FIG. 7, the control part 100 is connected to: the release buttons 32 for releasing the above-described arm 13 from being fixed; the sensor 36 for detecting that the X-ray detector 16 has been taken out of the storage part 17; the electro permanent magnets 41 and 42 for inhibiting the arm 13 from moving up or down, or turning; and the potentiometer 47 for detecting the height position of the arm 13. Further, the control part 100 includes an up and down control part 101 that when the sensor 36 detects that the X-ray detector 16 has been taken out of the storage part 17, releases the arm 13 from being fixed by the electro permanent magnets 41 and 42.

In the X-ray imaging apparatus for rounds having such a configuration, when an operator operates the operation handle 19 to move the cart 15, the arm 13 is arranged at the fixing position where the lower surface of the arm 13 comes into abut with the fixing part 18, as indicated by the solid line in FIG. 1. At this time, the action of the up and down control part 101 illustrated in FIG. 7 brings the coils 73 in the electro permanent magnets 41 and 42 into a state where no currents flows. For this reason, these electro permanent magnets 41 and 42 respectively function as magnets by the actions of the permanent magnets 71, and therefore the electro permanent magnet 41 sticks fast to the fixing part 18, whereas the electro permanent magnet 42 sticks fast to the stopper plate 43. As a result, the arm 13 is restricted from moving from the fixing position. Thus, in the case of moving the X-ray imaging apparatus among hospital rooms and the like, the X-ray imaging apparatus can be moved in a secure state with the arm 13 fixed at the fixing position.

When an operator takes the X-ray detector 16 out of the storage part 17 in order to take X-ray images after moving the X-ray imaging apparatus to an imaging location, the sensor 36 for confirming whether or not the X-ray detector 16 is present senses this and transmits to the up and down control part 101 a signal indicating that the X-ray detector 16 has been taken out of the storage part 17. Upon receipt of the signal, the up and down control part 101 applies currents to the coils 73 in the electro permanent magnets 41 and 42 to make the electromagnets generate the magnetic forces that cancel out the magnetic forces of the permanent magnets 71, respectively. In doing so, the braking force by the actions of the permanent magnets 71 is released, and sticking forces of the electro permanent magnets 41 and 42 on the fixing part 18 and the stopper plate 43 are released, respectively. As a result, the arm 13 is released from the restriction of movement from the fixing position.

Since the weight of the counter weight 45 is one larger than the total value of the weights of the arm 13, X-ray tube 11, collimator 12, and the like, in a state where the arm 13 is released from being fixed by the electro permanent magnets 41 and 42, the arm 13 starts to move up from the fixing position together with the X-ray tube 11 and the collimator 12 by the action of gravity on the counter weight 45. On the other hand, when the height position of the arm 13 detected by the potentiometer 47 adapted to function as a height position detector for the arm 13 reaches a preset predetermined height position, the up and down control part 101 again stops applying the currents to the coils 73 in the electro permanent magnets 41 and 42, respectively. In doing so, the electro permanent magnet 42 sticks fast to the stopper plate 43, and thereby the arm 13 is fixed at the height position.

Then, by arranging the X-ray detector 16 below an imaging region of a subject, and also as indicated by a virtual line in FIG. 2, turning the arm 13 to an angle that faces the X-ray detector 16 and is suitable for X-ray imaging, X-ray images can be taken.

In addition, in the X-ray imaging apparatus, not only in the case where an operator takes the X-ray detector 16 out of the storage part 17, but also in the case where an operator presses the release buttons 32 for releasing fixation of the arm 13, the sticking force of the electro permanent magnet 41 on the fixing part 18, and the sticking force of the electro permanent magnet 41 on the stopper plate 43 are released. For this reason, in the case where it is necessary to move the arm 13 up and down at a time other than X-ray imaging, the arm 13 can be moved up and down without taking the X-ray detector 16 out of the storage part 17.

As described above, in the X-ray imaging apparatus according to the present invention, since when the sensor 36 detects that the X-ray detector 16 has been taken out of the storage part 17, the action of the up and down control part 101 releases the arm 13 from being fixed by the electro permanent magnets 41 and 42, and also the action of the arm driving mechanism including the counter weight 45 moves up the arm 13 to the predetermined height together with the X-ray tube 11 and the collimator 12, X-ray imaging can be quickly prepared.

In addition, in the above-described first embodiment, when the height position of the arm 13 detected by the potentiometer 47 reaches the preset predetermined height position, the up and down control part 101 fixes the arm 13 by the action of the electro permanent magnet 42. As a variation of the first embodiment, a configuration where after a certain time has passed since the up and down control part 101 released the arm from being fixed by the electro permanent magnets 41 and 42, the up and down control part 101 again fixes the arm 13 by the action of the electro permanent magnet 42 may be employed. In this case as well, the arm 13 can be moved up to the predetermined height together with the X-ray tube 11 and the collimator 12.

Figure 8:
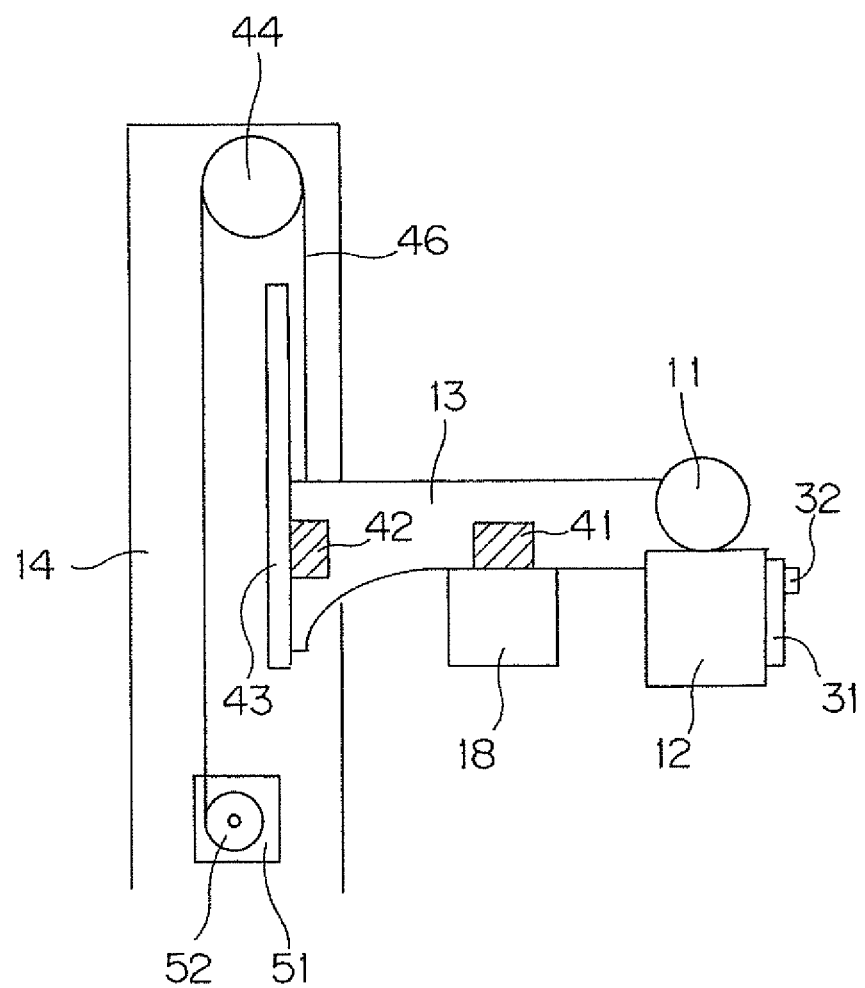
FIG. 8 is a schematic diagram illustrating an arm driving mechanism for moving up the arm 13 and a fixing mechanism for fixing the arm 13, both of which are according to a second embodiment of the present invention and employed for the X-ray imaging apparatus.
Figure 9:
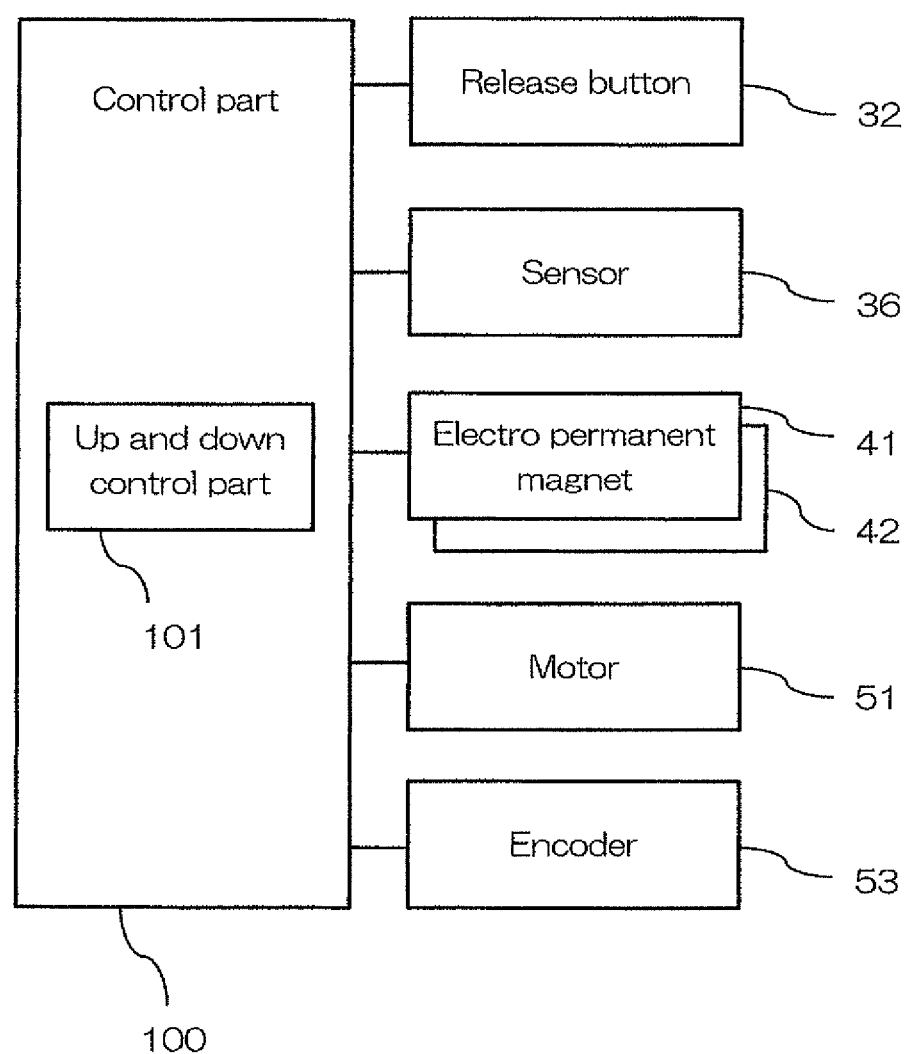
FIG. 9 is a block diagram illustrating a main control system of the X-ray imaging apparatus according to the second embodiment of the present invention.

Next, another embodiment of the present invention is described. FIG. 8 is a schematic diagram illustrating an arm driving mechanism for moving up the arm 13 and a fixing mechanism for fixing the arm 13, both of which are according to the second embodiment of the present invention and employed for the X-ray imaging apparatus. Also, FIG. 9 is a block diagram illustrating a main control system of the X-ray imaging apparatus according to the second embodiment of the present invention. Note that the same members as those in the above-described first embodiment are denoted by the same reference signs, and detailed description thereof is omitted.

The arm driving mechanism according to the above-described first embodiment is adapted to move up the arm 13 using the counter weight 45 having the larger weight than the total value of the weights of the arm 13, X-ray tube 11, collimator 12, and the like. On the other hand, the arm driving mechanism according to the second embodiment is adapted to move up and down the arm 13 by driving a motor 51, and also measure the height position of the arm 13 by an encoder 53.

The arm driving mechanism according to the second embodiment includes: the pulley 44: that is rotatably disposed at the upper end inside the supporting post 14; the motor 51 that is connected to a pulley 52; the encoder 53 (see FIG. 9) that detects a rotation amount of the pulley 52; and the wire 46 of which one end is connected to the arm 13 and the other end is wound around the pulley 44 in a state of being connected to the pulley 52. Note that in place of the wire 46, another cable such as a belt or a chain may be used.

In the X-ray imaging apparatus according to the second embodiment as well, when an operator takes the X-ray detector 16 out of the storage part 17 in order to take X-ray images, sticking force of the electro permanent magnet 41 on the fixing part 18, and sticking force of the electro permanent magnet 42 on the stopper plate 43 are released, and consequently the arm 13 is released from the restriction of movement from a fixing position.

Then, by controlling rotation of the motor 51 after releasing the arm 13 from being fixed by the electro permanent magnets 41 and 42, the up and down control part 101 moves up the arm 13 together with the X-ray tube 11 and the collimator 12 from the fixing position. When the height position of the arm 13 detected by the encoder 53 adapted to function as a height position detector for the arm 13 reaches a preset predetermined height position, the up and down control part 101 again stops applying currents to the coils 73 in the electro permanent magnets 41 and 42, respectively. In doing so, the electro permanent magnet 42 sticks fast to the stopper plate 43, and thereby the arm 13 is fixed at the height position.

In any of the above-described embodiments, the pair of electro permanent magnets 41 and 42 fixes the arm 13. However, the one electro permanent magnet 41 may be omitted. Alternatively, in place of the electro permanent magnets 41 and 42, a mechanical stopper capable of switching a fixing state, such as a solenoid, may be used.

Also, in any of the above-described embodiments, the storage part 17 of a box type adapted to insert the X-ray detector 16 from above to store the X-ray detector 16 is employed; however, the shape of the storage part 17 is not limited to this. For example, a storage part adapted to store the X-ray detector 16 in a hanging manner may be employed. It is only necessary that the storage part according to the present invention is configured to be able to store the X-ray detector 16 in some manner, and the storage detector is configured to be able to detect that the X-ray detector 16 has been taken out of the storage part.

REFERENCE SIGNS LIST

11 X-ray tube
12 Collimator
13 Arm
14 Supporting post
15 Cart
16 X-ray detector
17 Storage part
18 Fixing part
21 Front wheel
22 Rear wheel
32 Release button
36 Sensor
41 Electra permanent magnet
42 Electra permanent magnet
43 Stopper plate
44 Pulley
45 Counter weight
46 Wire
47 Potentiometer
51 Motor
52 Pulley
53 Encoder
100 Control part
101 Up and down control part

The invention claimed is:

1. An X-ray imaging apparatus, comprising: a cart; a supporting post that is disposed on the cart; an arm that is movable up and down along the supporting post; an X-ray tube that is disposed on the arm; an X-ray detector that detects an X-ray that is irradiated from the X-ray tube and passes through a subject; and a storage part for the X-ray detector, the X-ray imaging apparatus comprising:
   a fixing mechanism that fixes the arm at a fixing position that is a position where the arm should be arranged when moving the cart and lower than a height position where an X-ray image is taken;
   a storage detector that detects that the X-ray detector has been taken out of the storage part; and
   an up and down control part that when the storage detector detects that the X-ray detector has been taken out of the storage part, releases the arm from being fixed by the fixing mechanism.

2. The X-ray imaging apparatus according to claim 1, comprising
   an arm driving mechanism that when the arm is released from being fixed by the fixing mechanism, moves up the arm from the fixing position.

3. The X-ray imaging apparatus according to claim 2, further comprising
   a collimator that is disposed on the arm, wherein
   the arm driving mechanism comprises: a pulley that is disposed in the supporting post; a counter weight that has weight larger than a total value of weights of the arm, the X-ray tube, and the collimator; and a cable that is wound around the pulley, and has one end connected to the arm and the other end connected to the counter weight.

4. The X-ray imaging apparatus according to claim 3, further comprising
   a height position detector that detects a height position of the arm, wherein
   after the up and down control part has released the arm from being fixed by the fixing mechanism, when the height position of the arm reaches a predetermined position, the height position being detected by the height position detector, the up and down control part again fixes the arm by the fixing mechanism.

5. The X-ray imaging apparatus according to claim 3, wherein
   after a certain time has passed since the up and down control part released the arm from being fixed by the fixing mechanism, the up and down control part again fixes the arm by the fixing mechanism.

6. The X-ray imaging apparatus according to claim 2, wherein:
   the arm driving mechanism comprises a motor that drives the arm up and down; and
   when the arm is released from being fixed by the fixing mechanism, the up and down control part moves up the arm from the fixing position a predetermined distance by controlling rotation of the motor.

7. The X-ray imaging apparatus according to claim 6, wherein the fixing mechanism comprises an electro permanent magnet mechanism that comprises a permanent magnet and an electromagnet, and by generating braking force against up and down movement of the arm with use of magnetic force of the permanent magnet, and also applying current to a coil of the electromagnet to thereby make the electromagnet generate magnetic force that cancels out the magnetic force of the permanent magnet, releases the braking force against the up and down movement of the arm by the permanent magnet.

8. The X-ray imaging apparatus according to claim 5, wherein the fixing mechanism comprises an electro permanent magnet mechanism that comprises a permanent magnet and an electromagnet, and by generating braking force against up and down movement of the arm with use of magnetic force of the permanent magnet, and also applying current to a coil of the electromagnet to thereby make the electromagnet generate magnetic force that cancels out the magnetic force of the permanent magnet, releases the braking force against the up and down movement of the arm by the permanent magnet.

9. The X-ray imaging apparatus according to claim 4, wherein:

the fixing mechanism comprises an electro permanent magnet mechanism that comprises a permanent magnet and an electromagnet, and by generating braking force against up and down movement of the arm with use of magnetic force of the permanent magnet, and also applying current to a coil of the electromagnet to thereby make the electromagnet generate magnetic force that cancels out the magnetic force of the permanent magnet, releases the braking force against the up and down movement of the arm by the permanent magnet.

10. The X-ray imaging apparatus according to claim 1, wherein:

the fixing mechanism comprises an electro permanent magnet mechanism that comprises a permanent magnet and an electromagnet, and by generating braking force against up and down movement of the arm with use of magnetic force of the permanent magnet, and also applying current to a coil of the electromagnet to thereby make the electromagnet generate magnetic force that cancels out the magnetic force of the permanent magnet, releases the braking force against the up and down movement of the arm by the permanent magnet.

* * * * *